US008241316B2

(12) United States Patent
Oberle

(10) Patent No.: US 8,241,316 B2
(45) Date of Patent: Aug. 14, 2012

(54) INFLATABLE NASOPHARYNGEAL STENT

(76) Inventor: Paul Oberle, Ballwin, MO (US)

( * ) Notice: Subject to any disclaimer, the term of this patent is extended or adjusted under 35 U.S.C. 154(b) by 780 days.

(21) Appl. No.: 12/150,174

(22) Filed: Apr. 25, 2008

(65) Prior Publication Data
US 2009/0266365 A1   Oct. 29, 2009

(51) Int. Cl.
*A61M 29/00*   (2006.01)
(52) U.S. Cl. .................. 606/196; 128/848; 606/199
(58) Field of Classification Search .............. 606/196, 606/199, 191, 192, 198, 194, 108; 623/9, 623/1.11, 1.12, 1.13, 1.14, 1.15, 1.16, 1.17, 623/1.18; 604/22, 45, 97.01, 96.01; 128/207.18, 128/200.14, 207.14, 848
See application file for complete search history.

(56) References Cited

U.S. PATENT DOCUMENTS

| | | | |
|---|---|---|---|
| 2,525,183 A | 10/1950 | Robison | |
| 4,457,756 A | 7/1984 | Kern et al. | |
| 4,883,465 A * | 11/1989 | Brennan | 604/96.01 |
| 5,139,510 A | 8/1992 | Goldsmith, III et al. | |
| 5,496,365 A * | 3/1996 | Sgro | 623/1.2 |
| 5,776,160 A * | 7/1998 | Pasricha et al. | 606/191 |
| 6,159,158 A | 12/2000 | Lowe | |
| 6,183,493 B1 | 2/2001 | Zammit | |
| 6,328,753 B1 | 12/2001 | Zammit | |
| 6,394,093 B1 * | 5/2002 | Lethi | 128/207.18 |
| 6,450,989 B2 | 9/2002 | Dubrul et al. | |
| 6,607,546 B1 * | 8/2003 | Murken | 606/196 |
| 6,814,749 B2 | 11/2004 | Cox et al. | |
| 7,108,706 B2 * | 9/2006 | Hogle | 606/199 |
| 2004/0020492 A1 * | 2/2004 | Dubrul et al. | 128/207.18 |
| 2005/0027247 A1 | 2/2005 | Carrison et al. | |
| 2005/0060023 A1 * | 3/2005 | Mitchell et al. | 623/1.15 |
| 2005/0124849 A1 | 6/2005 | Barbut et al. | |
| 2005/0171564 A1 * | 8/2005 | Manzo | 606/153 |
| 2005/0240147 A1 | 10/2005 | Makower et al. | |
| 2006/0004323 A1 | 1/2006 | Chang et al. | |
| 2006/0149310 A1 | 7/2006 | Becker | |
| 2007/0129751 A1 | 6/2007 | Muni et al. | |
| 2007/0179518 A1 * | 8/2007 | Becker | 606/199 |
| 2008/0053458 A1 * | 3/2008 | De Silva et al. | 128/207.18 |
| 2010/0217302 A1 | 8/2010 | Oberle | |

OTHER PUBLICATIONS

Co-pending U.S. Appl. No. 12/390,173, filed Feb. 20, 2009.
Office Action dated Nov. 1, 2011 from co-pending U.S. Appl. No. 12/390,173.

* cited by examiner

*Primary Examiner* — Gary Jackson
*Assistant Examiner* — Katrina Stransky
(74) *Attorney, Agent, or Firm* — Evans & Dixon, LLC; Don V. Kelly

(57) ABSTRACT

An inflatable nasopharyngeal stent is disclosed along with a method of using same. The stent comprises a central tube having a lumen defining a central inner chamber. A plurality of inflatable spokes are disposed along the central tube. The spokes are in fluid communication with the inner chamber of the central tube and are preferably aligned in groupings along the central tube. The outer ends of the spokes connect to a rib. The un-inflated stent is inserted into the nasal passageway through a naris and positioned such that so that a portion of the device is proximal to an anatomic structure exhibiting undesirable inflammation, configuration, growth or motility. Once positioned, the stent is inflated. Upon inflation, the ribs and adjoining web members move outwardly from the central tube and press upon the tissues of the nasopharyngeal cavity. Spaces between the inflatable spokes permit the passage of air along the stent and maintain airway patency.

13 Claims, 13 Drawing Sheets

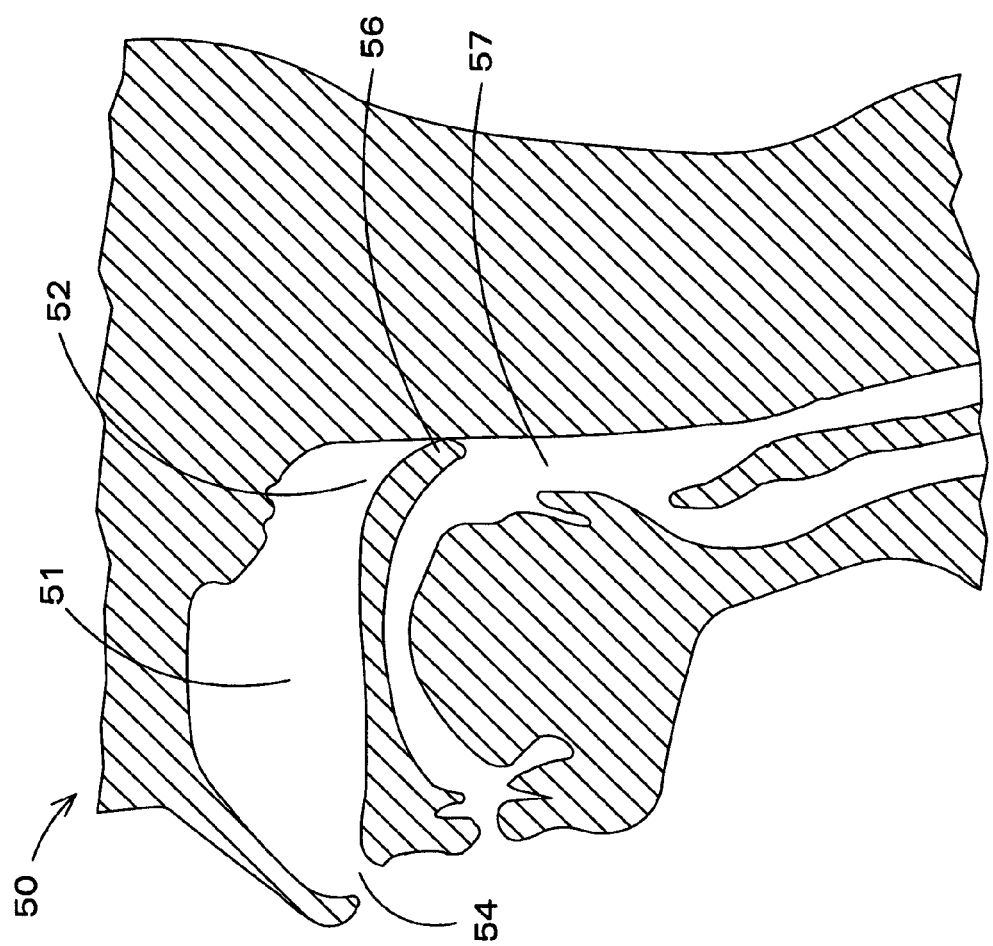

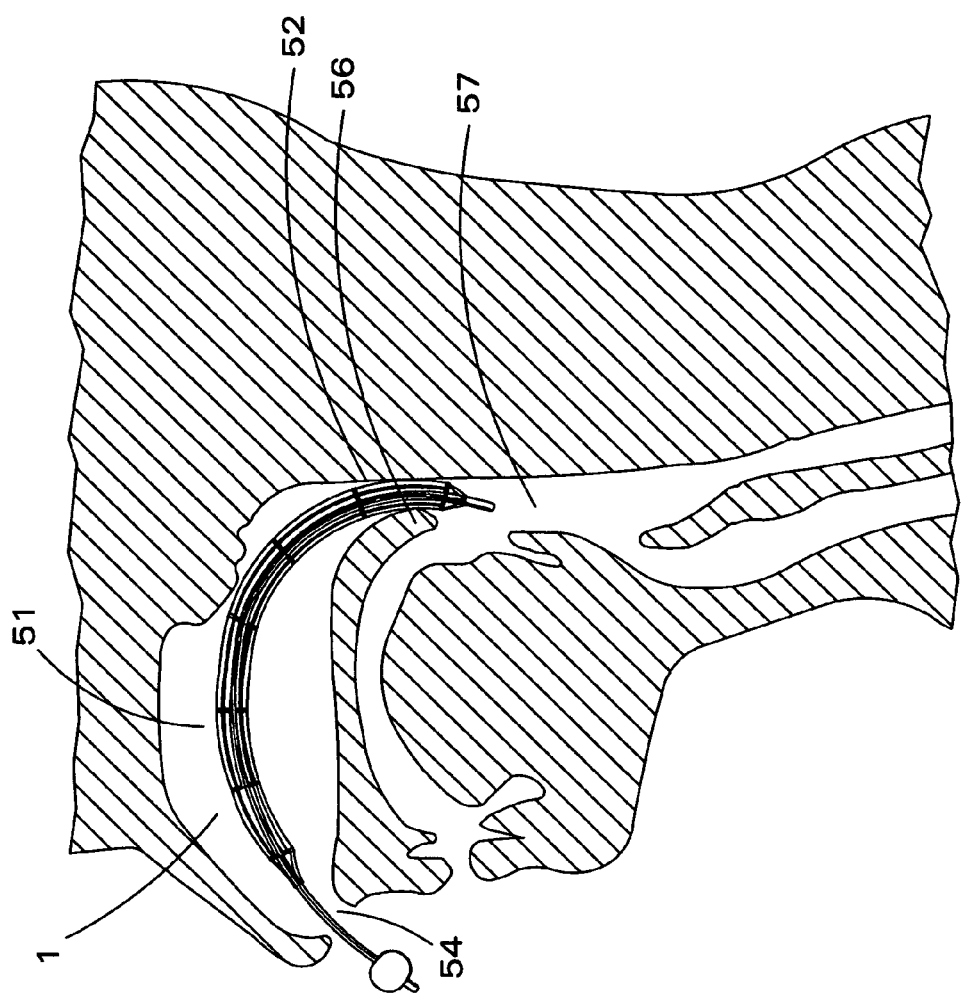

INFLATABLE NASOPHARYNGEAL STENT

CROSS REFERENCE TO RELATED APPLICATION

Not applicable.

STATEMENT REGARDING FEDERALLY SPONSORED RESEARCH OR DEVELOPMENT

Not applicable.

SEQUENCE LISTING TABLE OR COMPUTER PROGRAM OR COMPACT DISC

Not applicable.

FIELD OF THE INVENTION

This invention relates generally to methods and devices for treating nasopharyngeal obstructions and maintaining nasopharyngeal airway patency. More specifically, this invention relates to an improved method and apparatus for treating sleep apnea and breathing disorders caused by undesirable inflammation, configuration, growth or motility of nasopharyngeal structures.

BACKGROUND OF THE INVENTION

An apnea is a period of time during which breathing stops or is markedly reduced. In simplified medical terms, an apnea occurs when a person stops breathing for 10 seconds or more. Apneas usually occur during sleep. Sleep apnea is a disorder characterized by a reduction or cessation of breathing airflow during sleep. A reduction or cessation of airflow during sleep causes a resultant drop in blood oxygen level. This reduced blood oxygen level is detected by the brain, which sends out a signal to the body to wake up and take a breath. Consequently, when an apnea occurs, sleep is disrupted. Sometimes this means the person wakes up completely, but sometimes this can mean the person comes out of a deep level of sleep and into a more shallow level of sleep.

There are two basic types of sleep apnea: central sleep apnea and obstructive sleep apnea. Of the two types, obstructive sleep apnea is more common. Central sleep apnea occurs when the brain does not send the signal to the muscles to take a breath, and there is no muscular effort to take a breath. Obstructive sleep apnea occurs when the brain sends the signal to the muscles and the muscles make an effort to take a breath, but they are unsuccessful because the airway becomes obstructed and prevents the flow of air. In some instances, a patient may have both forms of sleep apnea, in which case the patient is considered to have "mixed apnea."

Obstructive sleep apnea is estimated to affect about 4% of men and 2% of women. The prevalence of obstructive sleep apnea can be correlated to obesity within a population as obesity exacerbates obstructive sleep apnea. Some studies suggest that among obese patients, upwards of 70% have obstructive sleep apnea. Obstructive sleep apnea can cause or exacerbate existing conditions of high blood pressure, stroke, extreme daytime sleepiness, ischemic heart disease, insomnia and mood disorders. In addition, patients with obstructive sleep apnea who receive sedation, analgesia or anesthesia for diagnostic or therapeutic procedures are at increased risk for perioperative complications.

During sleep in a person not having obstructive sleep apnea, air passes through the nasal passages, behind the palate, uvula, and tongue base, through the throat muscles, between the vocal cords and into the lungs. With obstructive sleep apnea, undesirable growth, configuration, swelling or motility of the nasal passages, palate, tongue, and pharyngeal tissues can all contribute to narrowing of the airway. In some cases, people with obstructive sleep apnea have an airway that is more narrow than normal, usually at the base of the tongue and palate. When lying flat, the palate is above the air passage. As shown in FIG. 11, in an apneic patient, when the pharyngeal muscles relax, the palate can fall backwards. Similarly, relaxation of the genioglossus muscle during sleep allows the base of the tongue to fall backwards, and the airway closes. These events can obstruct the airway. In many case the tissues of the airway are often sucked together by the negative pressure of air traveling into the lungs. This tissue action can exacerbate the degree of obstruction because the harder the chest tries to pull air in, the greater the negative pressure, and the more the tissues of the airway are sealed together.

The treatment of obstructive sleep apnea may be either surgical or nonsurgical. Surgical options for sleep apnea, however, may involve extended time off from work to heal and painful recoveries. Surgical options are also dependent on an individual's specific anatomy and severity of sleep apnea. Surgical options for treatment of obstructive sleep apnea include nasal airway surgery, palate implants, uvulopalatopharyngoplasty, tongue reduction, genioglossus advancement, hyoid suspension, maxillomandibular procedures, tracheostomy and bariatric surgery. Because these surgeries carry risk and offer no guarantee of improvement, most patients with obstructive sleep apnea go through a regimen of non-surgical treatments before considering surgery. Non-surgical treatments for obstructive sleep apnea include postural sleeping changes, dental appliances, medications (decongestants and steroid sprays) and use of CPAP (continuous positive airway pressure) devices.

CPAP is probably the best, non-surgical treatment for obstructive sleep apnea. A CPAP machine blows heated, humidified air through a short tube into a mask affixed to the patient's face. CPAP uses air pressure to hold airway tissues open during sleep. By delivering air through a nasal or facemask under pressure, as the patient breathes, the gentle pressure holds the nose, palate, and throat tissues open. The effectiveness of CPAP requires that the mask must be worn snugly to prevent the leakage of air. This is often difficult because of the discomfort engendered by masks. Critically, if the mask does not fit correctly, the efficacy of CPAP drops significantly. Also, when employing a CPAP machine, it is important to use the lowest possible pressure that will keep the airway open during sleep. However, a different pressure may be needed for different positions or levels of sleep. These pressure levels, however, must be determined in a clinical setting or require an "auto-titrating" feature on the CPAP machine. Hence another disadvantage of CPAP is that it is not always easy to use. Studies show that only 60% of people with CPAP machines actually use them. When actual use time is measured, only 45% of those patients that actually use the machines use them more than 4 hours per night. Between 25 and 50% of people who start using CPAP, stop using it.

Due to the compliance issues attendant to CPAP treatment modalities, other methods of maintaining airway patency have been proposed. In this regard, use of a nasopharyngeal tube has been proposed to maintain airway patency. Though originally designed for placement by a physician, some prior art airway maintenance devices are intended for nightly use at home by the patient. For instance U.S. Pat. No. 6,328,753 discloses a folded tube intended for insertion into a patient's nostril and into the nasal passage way. Using a tube, however, to maintain, biologic passageway patency has certain disadvantages. First, the tube must be made of a sufficiently rigid material to enable insertion into the oropharynx. The fact that the tube is constructed of such material and that the tube has a large surface area increases the possibility of irritating contact with body tissues. Similarly, the large surface area of the tube can interfere with the natural secretory functions of surrounding tissues and sinuses of the nasal cavities. Accordingly, a need exists for an improved patient-usable, nasopharyngeal patency device that eliminates or minimizes the deficits of prior art devices.

SUMMARY OF THE INVENTION

The invention herein is directed to an inflatable nasopharyngeal stent that maintains airway patency and a method of using same. The invention can be used to treat nasopharyngeal obstructions and sleep apnea in both the home and perioperative setting. As a home-use device, the stent can be placed into position by a patient before going to sleep. In the perioperative setting, medical personnel can utilize the device both during and after administration of sedatives, analgesics or anesthetics to reduce complications in apneic patients.

In a preferred embodiment the present invention device comprises an elongate central tube having a first (proximal end) end and second (distal) end. The distal end of the tube is closed and the proximal end includes inflation means. The lumen of the tube defines a central inner chamber adapted to retain a fluid such as air or a non-toxic gas or liquid. A plurality of inflatable spokes are disposed along the tube. The lumen of each spoke defines a spoke inner chamber, which is in fluid communication with the central inner chamber. In a preferred embodiment, the plurality of spokes are arranged on the central tube such that they form groupings of axially (lengthwise) or helically aligned spokes. Each grouping comprises at least two spokes. The spokes of each grouping are connected at their outer end to a perimeter rib. The present invention stent therefore comprises a plurality of ribs that preferably extend longitudinally along or helically about the central tube. Each rib has two ends. One end is the proximal end, which of the two rib ends is nearest the proximal end of the central tube. The other end is the distal end, which of the two rib ends is nearest the distal end of the central tube. Each rib has a preferred length at least that of the length of the grouping of ribs to which it is attached. In a preferred embodiment, an aligning lead extends from the distal end of each rib to the closed end of the central tube. In a preferred embodiment, an aligning lead also extends from the proximal end of each rib to a point on the central tube between the spoke closest the inflation means and the inflation means. One or more web members extend from each side of the rib to an adjacent rib. Preferably each web member contacts the rib at a point where a spoke meets the rib.

In a preferred embodiment, each spoke is made of a flexible and expandable material such that in the un-inflated (collapsed) state the spoke lies flaccidly upon the central tube. When an inflating fluid such as air is introduced into the central tube it fills the central tube and then via pressure enters into the spoke inner chamber of each spoke. The entry of fluid into the spoke inner chamber causes the spoke to move from its flaccid state, rigidify and extend radially outward from the central tube. Upon doing so, the inflated spoke will move the rib attached to it along with attached web members outwardly away from the central tube. In the preferred embodiment the fully inflated spoke will extend outwardly at an angle approximately normal to the central tube. When all spokes have inflated and are radially extended, spaces between the inflated spokes permit the easy passage of air along the length of the stent. The inter-spoke spaces of the preferred embodiment stent are wedge-shaped.

In use the collapsed (un-inflated) stent of the present invention is inserted through a naris and into the nasal passage way. The stent is typically fully inserted when the distal end of the stent is proximal to the soft palate structures. In cases where the obstruction is due to lingual collapse, the stent may be inserted into position where its distal end is proximal to and presses against the base of the tongue. In the full insertion mode a sufficient length of the proximal end of the stent extends out through the naris to permit manipulation and inflation of the stent. Once fully inserted, a portion of the stent is proximal to the anatomic structure or structures of the nasopharynx exhibiting undesirable inflammation, configuration, growth or motility. The stent can then be inflated and fixed into position. Inflation means at the proximal end of the central tube allows for the inflation of the stent and retention of inflating fluid. In its inflated state, the perimeter ribs and web members of the stent press outwardly against the tissue of the nasopharynx prohibiting their collapse or incursion into the airway. By virtue of the inter-spoke spaces, air may freely pass through the nasal passageway into the pharynx.

BRIEF DESCRIPTION OF THE DRAWINGS

FIG. 11 is a cross section view of a nasopharyngeal cavity in a patient with an apnea causing obstruction.

FIG. 12 is a cross section view of a nasopharyngeal cavity in which a preferred embodiment nasopharyngeal stent of the present invention is inserted in its un-inflated state.

DETAILED DESCRIPTION OF THE INVENTION

The present invention relates to an inflatable nasopharyngeal stent and method of using same. In its un-inflated state, the stent is insertable into the nasal passageway via one of the nares. Once fully inserted and positioned, the stent is inflated. Inflating the stent causes radial spokes bearing perimeter ribs to expand outwardly from the stent such that the ribs and their adjoining web members press against the tissues of the nasopharyngeal cavity that define the patient airway. The pressing force from the stent restricts tissue swelling, incursion or motility and therefore prevents the nasopharyngeal structures from collapsing or intruding into the airway. Inter-spoke spaces allow the flow of air along the length of the stent and result in airway patency.

A preferred embodiment present invention nasopharyngeal stent is shown in the inflated state in FIGS. 1-5. Stent 1 comprises central tube 2 having lumen 3. Central tube 2 is made from a biocompatible material that is: (a) rigid enough to allow the tube to be pushed through a curving biologic passageway, such as the nasopharynx; and (b) flexible enough to follow the contours of the passageway without damaging surrounding tissues. Suitable materials include, for example, nylon, PVC, polyurethane, polyethylene, and polypropylene.

Figure 4:
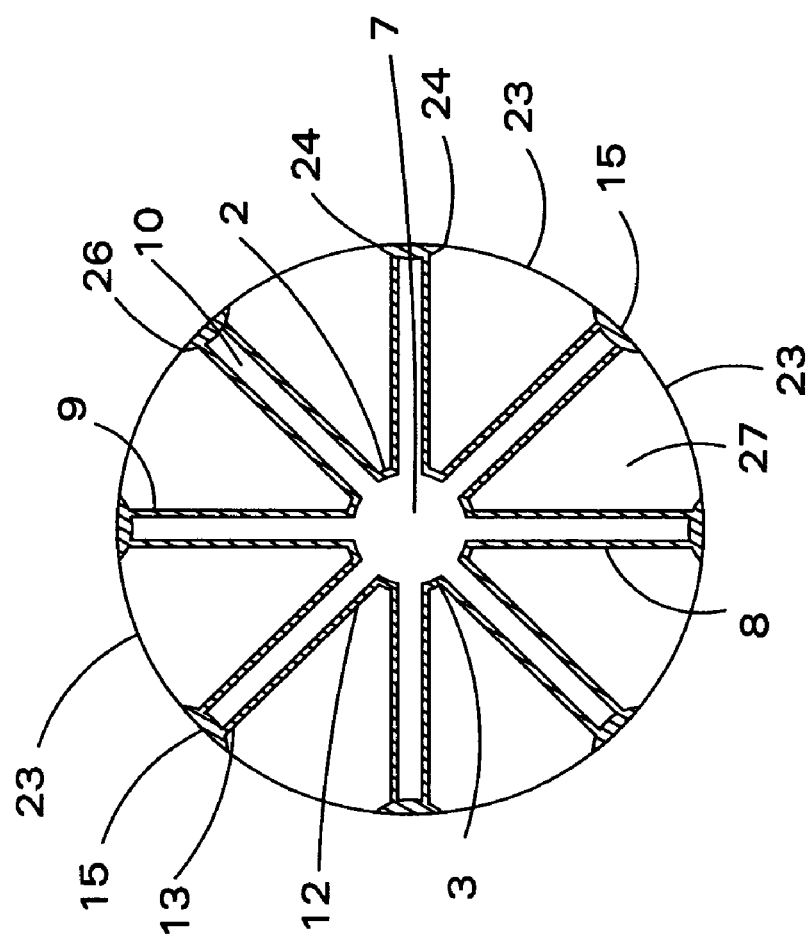
FIG. 4 is a cross section view taken along line A-A of FIG. 1 of a preferred embodiment nasopharyngeal stent of the present invention in the inflated state.
Figure 5:
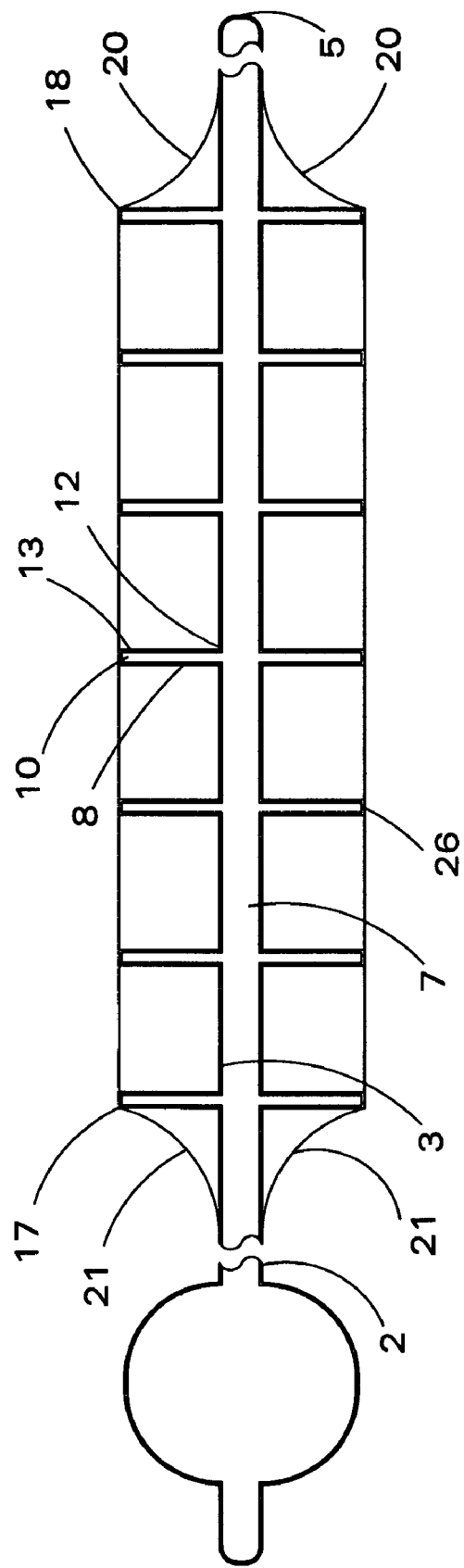
FIG. 5 is a cross section view taken along line B-B of FIG. 1 of a preferred embodiment nasopharyngeal stent of the present invention in the inflated state.

Central tube 2 has a proximal end 4 and distal end 5. Distal end 5 of tube 2 is closed. Proximal end 4 includes inflation (fluid introduction) means 6. As best seen in FIG. 4, lumen 3 of tube 2 defines a central inner chamber 7. Inner chamber 7 is in fluid communication with inflation means 6. A plurality of inflatable spokes 8 are disposed along tube 2. Each spoke comprises a lumen 9, an inner end 12 and an outer end 13. Spoke inner end 12 is connected to central tube 2. Lumen 9 of each spoke 8 defines a spoke inner chamber 10, which is in fluid communication with the central inner chamber 7. In a preferred embodiment, the plurality of spokes 8 are arranged on tube 2 such that they form one or more groupings 11 of axially or helically aligned spokes 8. Each grouping 11 comprises at least two spokes 8.

Figure 1:
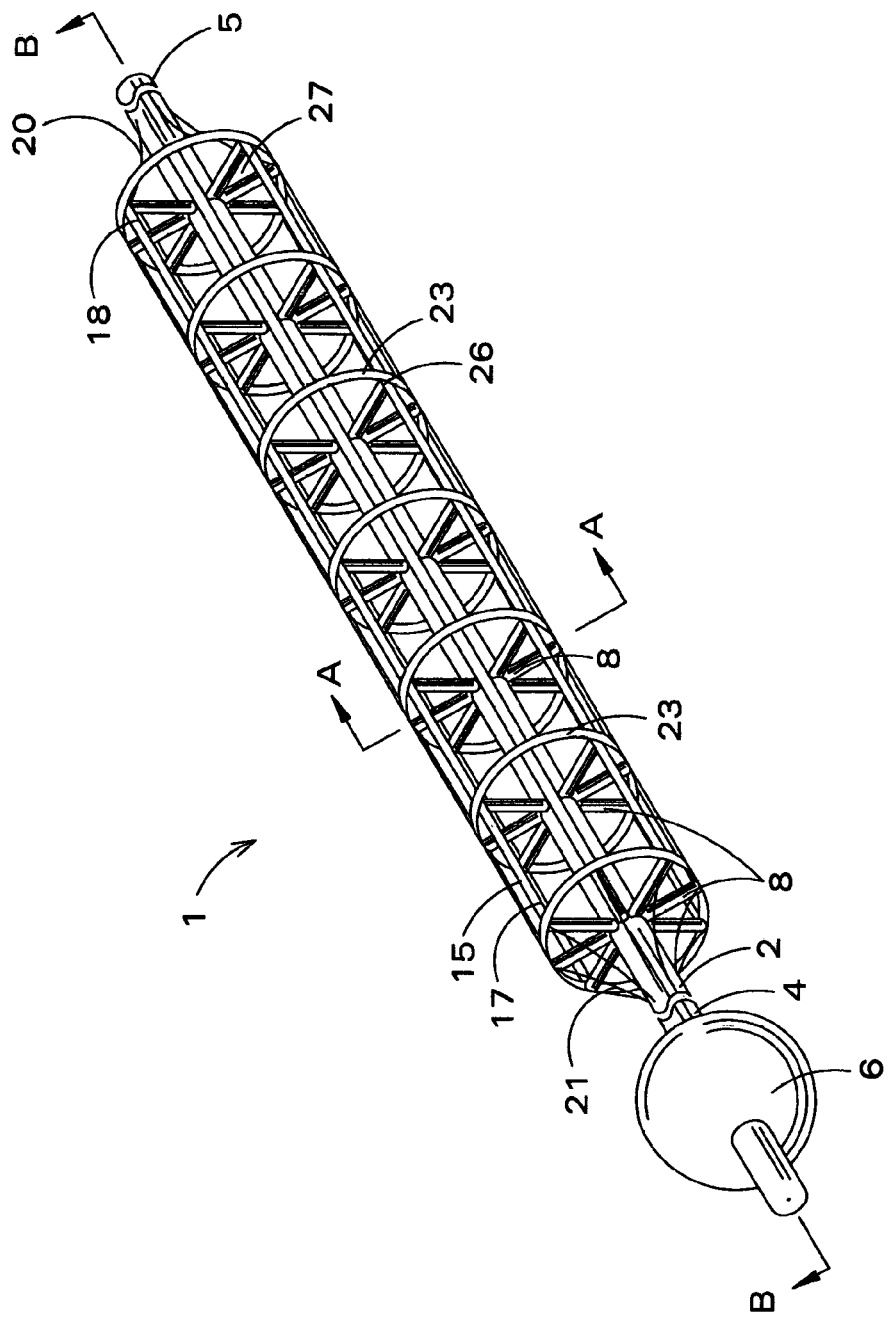
FIG. 1 is a perspective view of a preferred embodiment nasopharyngeal stent of the present invention in the inflated state.
Figure 2:
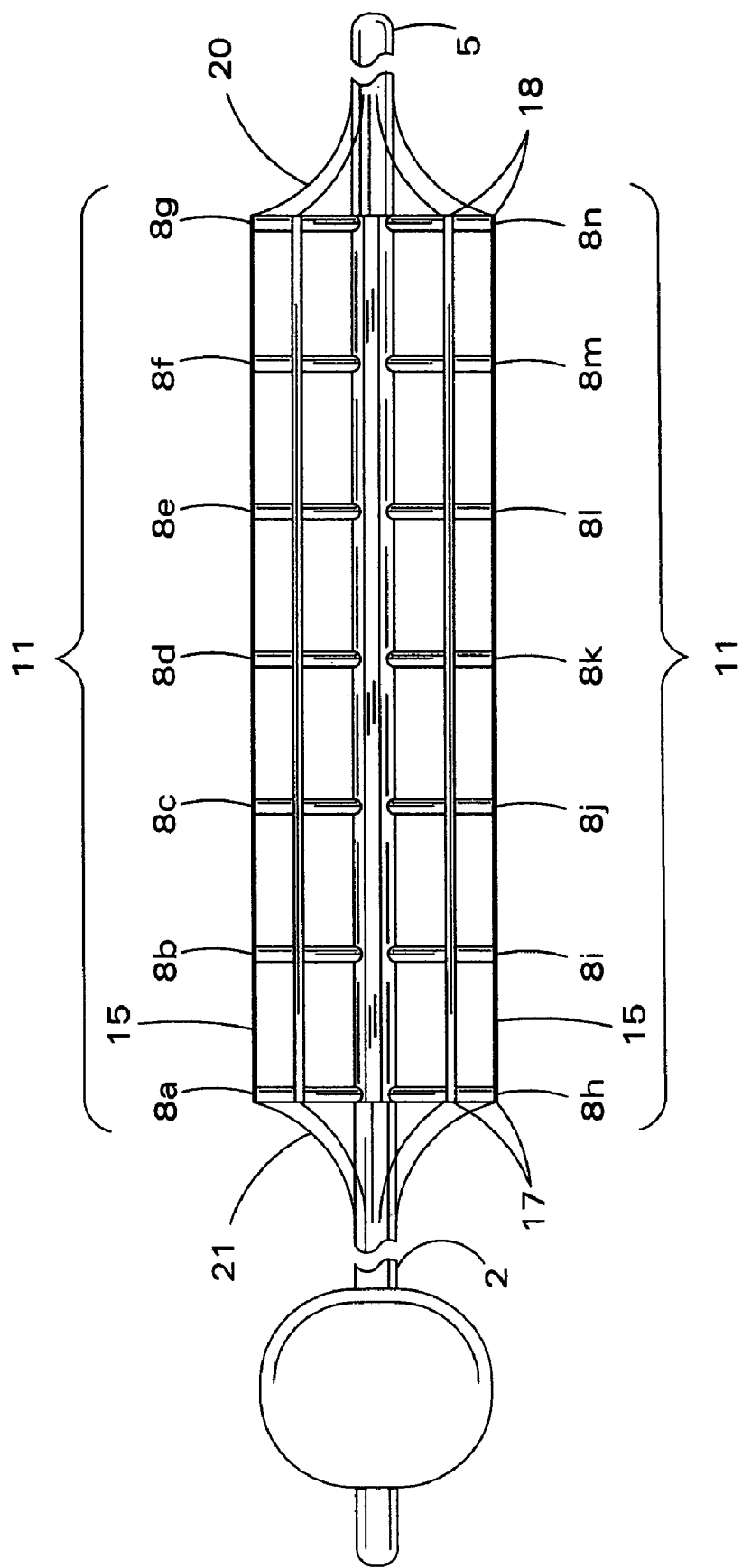
FIG. 2 is a side elevation view of a preferred embodiment nasopharyngeal stent of the present invention in the inflated state.
Figure 3:
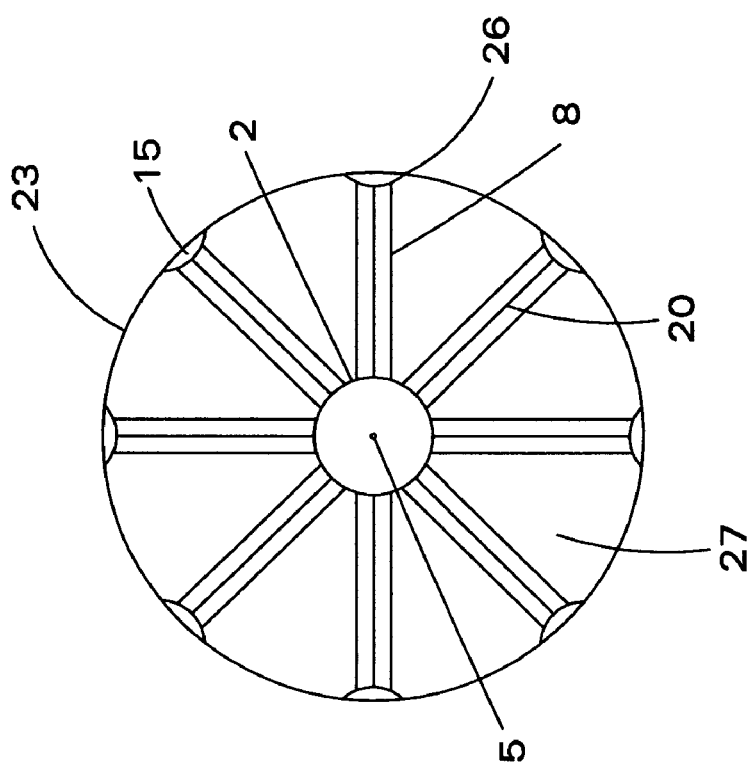
FIG. 3 is a distal end elevation view of a preferred embodiment nasopharyngeal stent of the present invention in the inflated state.

FIG. 2 depicts a preferred embodiment stent having spokes that are axially (length-wise) aligned along central tube 2. In FIG. 2, two spoke groupings of seven spokes (one group consisting of spokes 8a-8g and the other group consisting of spokes 8h-8n) are identified. In the depicted preferred embodiment, spokes 8 of each grouping 11 are connected at their outer end 13 to a rib 15 extending longitudinally (axially) along central tube 2 and running the length of the respective grouping 11. The un-inflated spokes of this embodiment lie flaccidly along central tube 2, preferably in an approximately longitudinal direction along the central tube. As used herein the term "approximately longitudinal" means within 20 degrees of the direction of the central tube. In an alternate embodiment, spokes 8 may be helically aligned in groupings 11 such that the spokes of each grouping are connected at their outer end 13 to a rib 15 that extends helically about central tube 2.

Stent 1 comprises a plurality of ribs 15. Each rib 15 has a proximal end 17 and distal end 18. In a preferred embodiment, a distal aligning lead 20 extends from distal end 18 of each rib 15 to closed end 5 of tube 2. In a preferred embodiment, a proximal aligning lead 21 extends from the proximal end 17 of each rib 15 to a point on tube 2 between the spoke 8 closest the inflation means 6 and the inflation means 6. One or more web members 23 extend from each side 24 of the perimeter rib 15 to an adjacent perimeter rib 15 and maintain the alignment of spokes 8 and their groupings 11. Preferably each web member 23 contacts the perimeter rib 15 at the point 26 where a spoke 8 meets the perimeter rib 15. In a preferred embodiment web members are made of a biocompatible flexible plastic or rubber compound.

Figure 6:
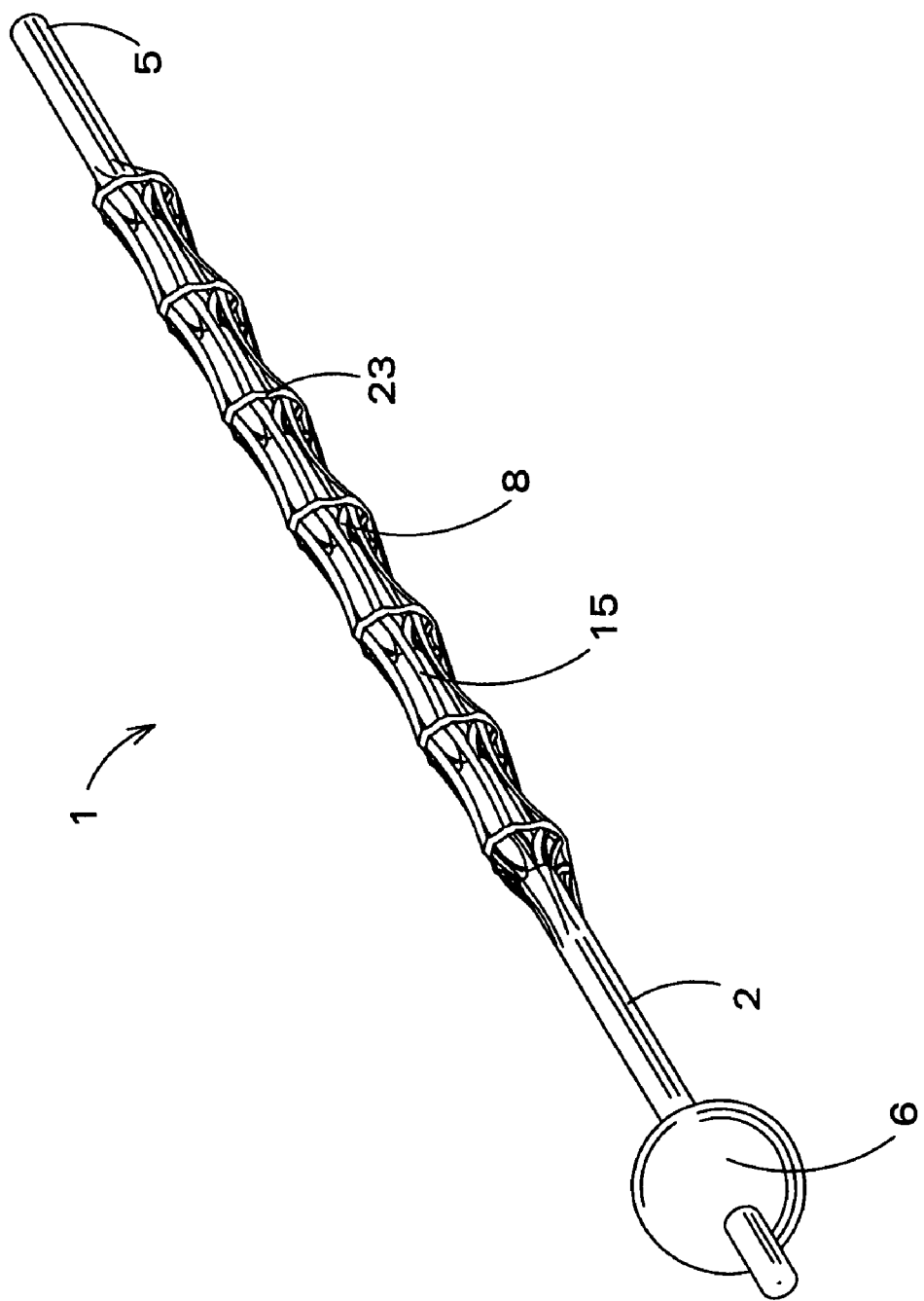
FIG. 6 is a perspective view of a preferred embodiment nasopharyngeal stent of the present invention in the un-inflated state.
Figure 7:
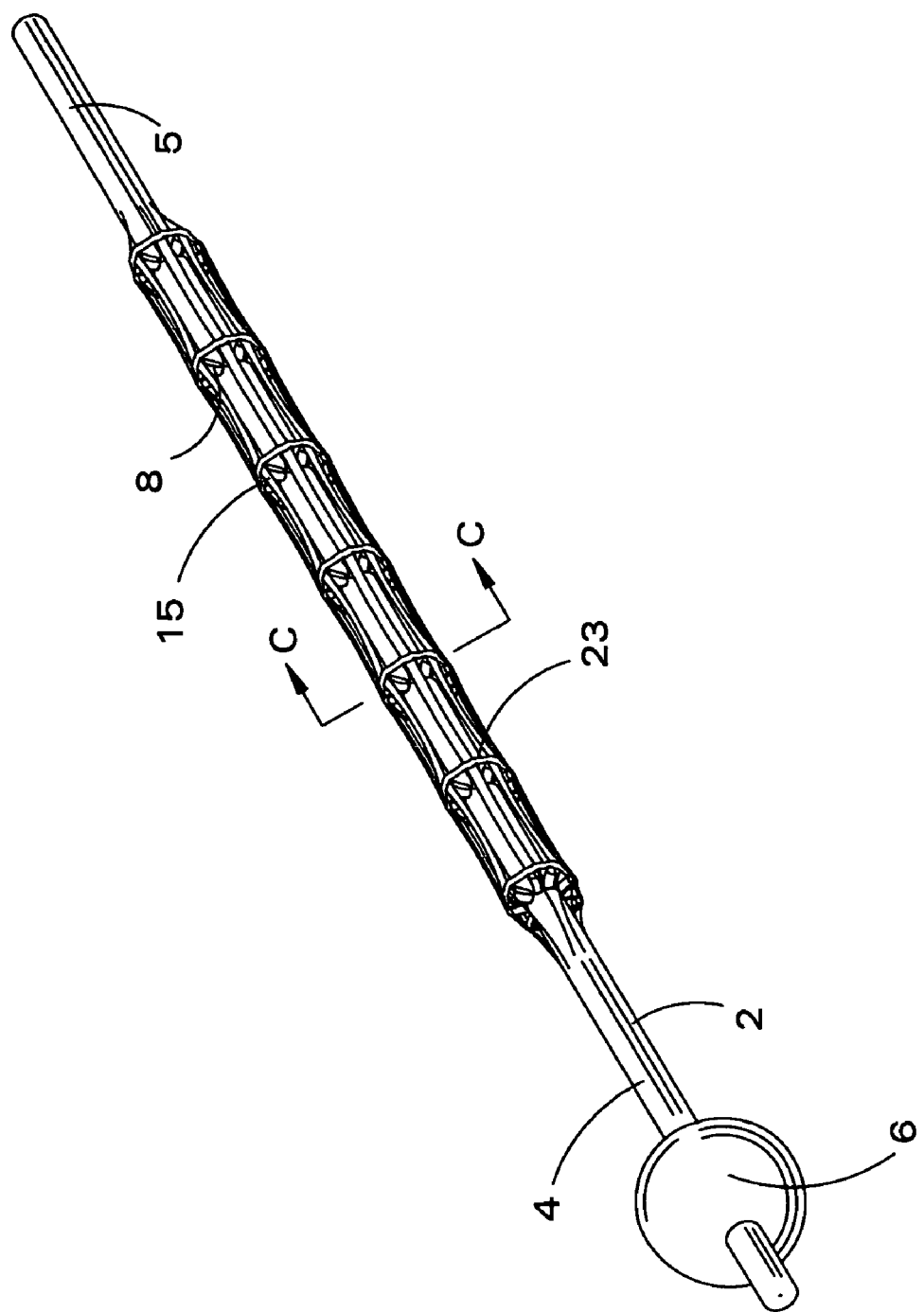
FIG. 7 is a perspective view of an alternate embodiment un-inflated nasopharyngeal stent of the present invention having folded-in, telescoping spokes.
Figure 8A:
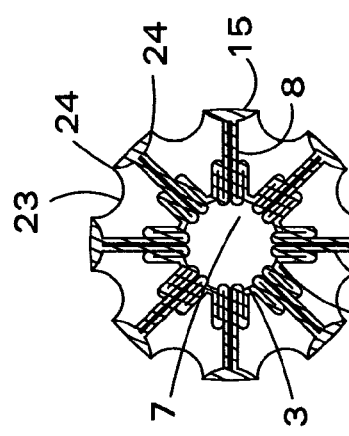
FIGS. 8a, 8b and 8c are cross section views taken along line C-C of the alternate embodiment nasopharyngeal stent of FIG. 7 depicting the stent changing from the un-inflated to inflated state.
Figure 8C:
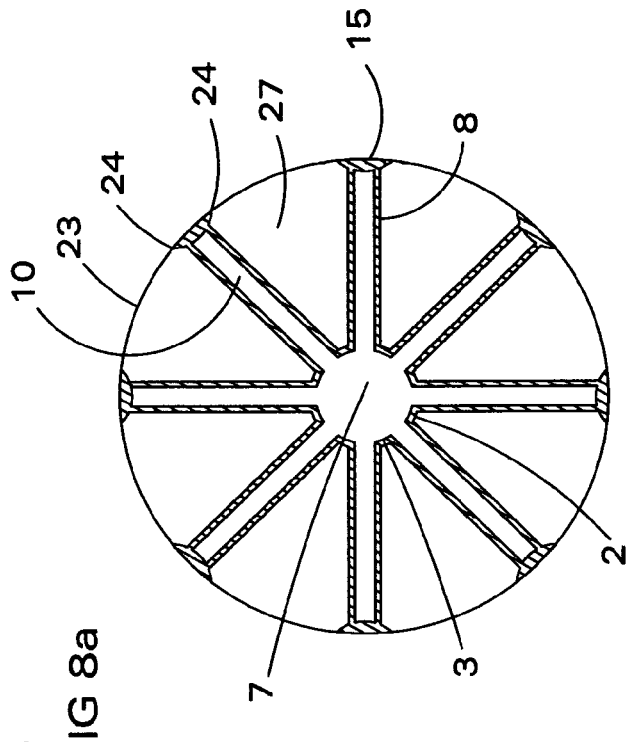
Figure 8B:
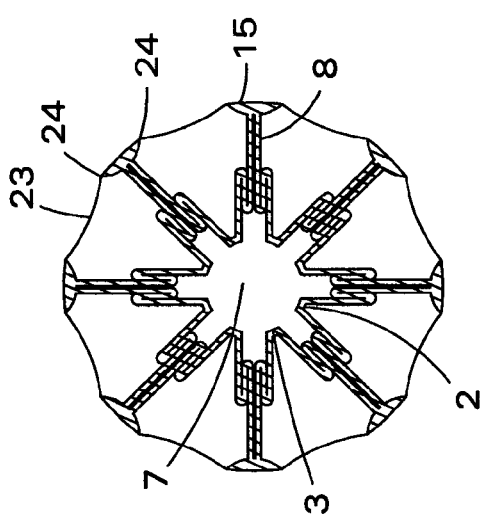

Each spoke 8 is made of a flexible and elastic material such that in the un-inflated state the spoke lies on central tube 2. Depending upon the chosen embodiment of the stent, the flaccid spokes will preferably extend in an approximate longitudinal direction or helical direction along central tube 2. Suitable spoke material includes an elastic rubber or plastic, for example, silicone rubber or polyether polyurethane. As shown in FIGS. 6 and 12, in the un-inflated state stent 1 is easily insertable through a patient's nasal passageway into the oropharynx. When an inflating fluid such as air is introduced under pressure into central tube 2 it fills central chamber 7 and then via pressure enters into the inner chamber 10 of each spoke 8. The entry of fluid into spoke inner chamber 10 causes spoke 8 to inflate and move from its flaccid position to a radially extending position, approximately normal to central tube 2. Ribs 15 are disposed upon the outer ends 13 of spokes 8. Hence, when all spokes 8 have inflated and are radially extended, ribs 15 and web members 23 are located outwardly remote from central tube 2. In a preferred embodiment, ribs 15 are made of a biocompatible soft but flexibly rigid material such as PVC, polyurethane, polypropylene or polyethylene to reduce irritation of the nasopharyngeal tissues. In an alternate embodiment, ribs 15 and web members 23 could be integral inflatable, fluidly connected extensions of spokes 8. Inter-spoke spaces 27, which in the preferred embodiment are wedge-shaped, are located between adjacent inflated spokes 8 and permit the easy passage of air along the length of the stent 1.

Figure 9:
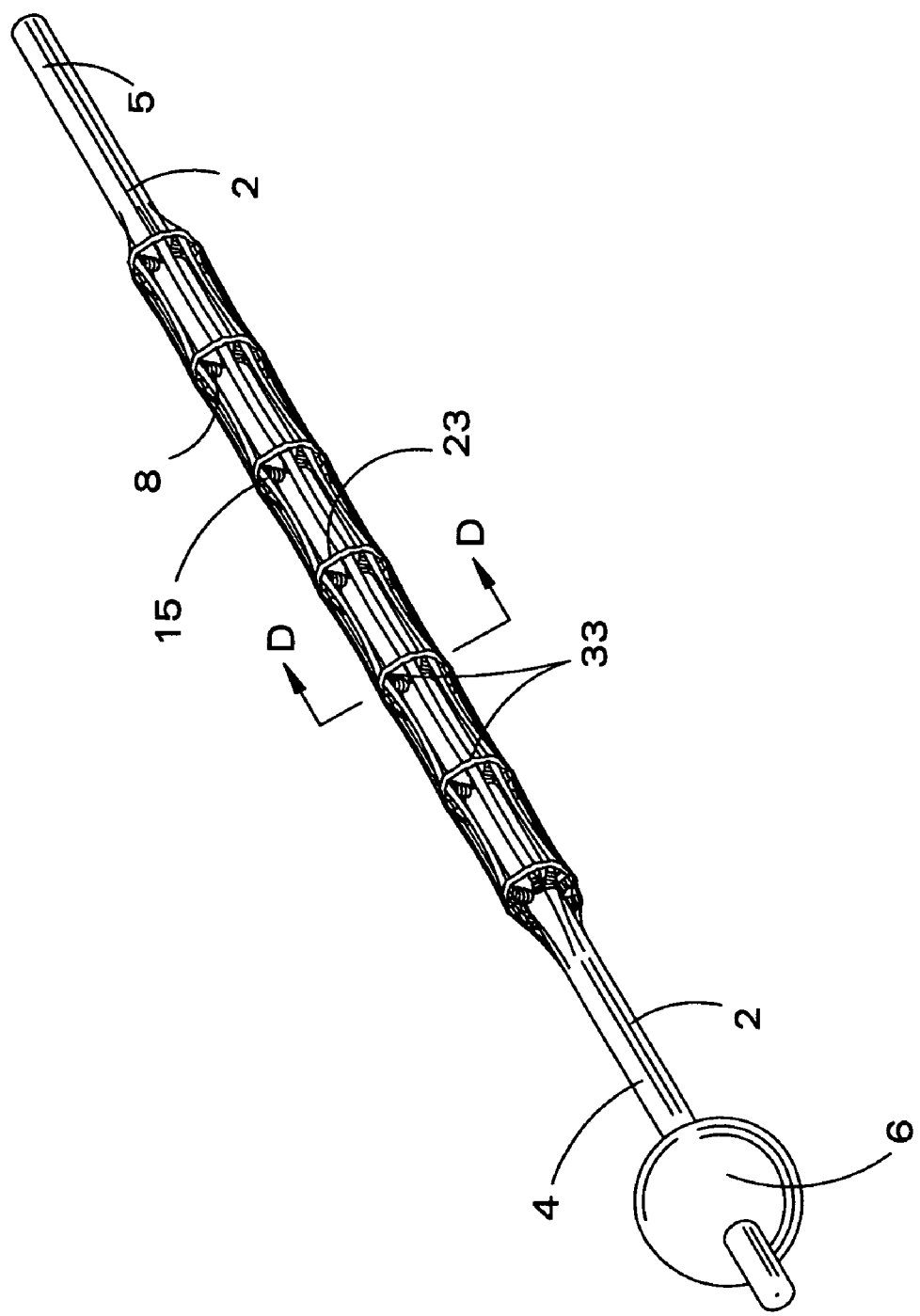
FIG. 9 is a perspective view of an alternate embodiment un-inflated nasopharyngeal stent of the present invention having accordiated (pleated) spokes.
Figure 10A:
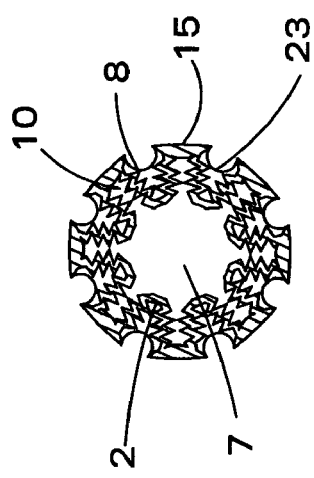
FIGS. 10a, 10b and 10c are cross section views taken along line D-D of the alternate embodiment nasopharyngeal stent of FIG. 9 depicting the stent changing from the un-inflated to inflated state.
Figure 10C:
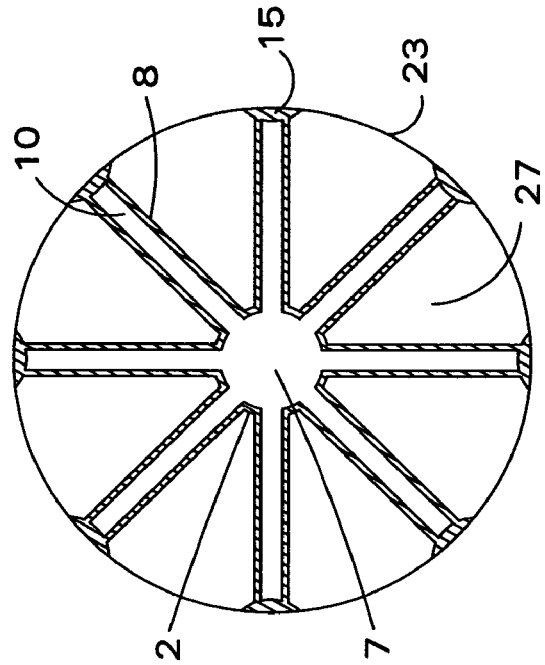
Figure 10B:
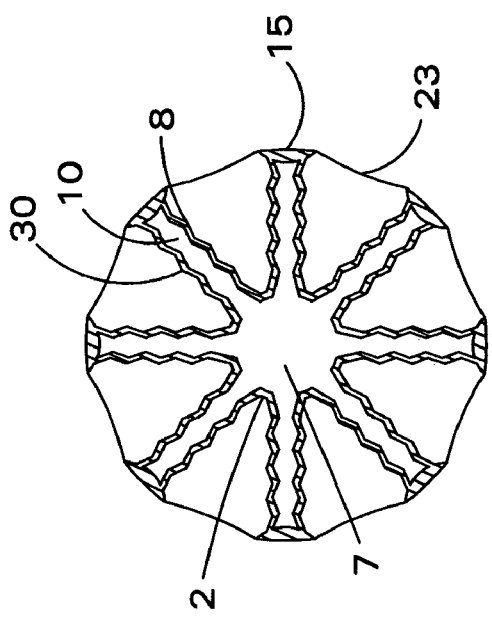

As shown in FIGS. 7-10, in an alternate embodiment, stent 1 can utilize an inflatable spoke 8 that can fold in upon itself (FIGS. 7, 8a, 8b, 8c) or have compressible, accordiated pleats (FIGS. 9, 10a, 10b, 10c). To enhance it folding ability or compressibility, spoke 8 can have a radial outermost end that tapers from the end affixed to central tube 2. As shown in FIGS. 7, 8a, 8b, and 8c, when spoke 8 is made foldable within itself, it can be telescopically compressed into central tube 2 to reduce the stent's diametric profile. As shown in FIGS. 8a, 8b and 8c, in the un-inflated state each spoke 8 is compressed downward into central tube 2. Upon inflation, compressed spoke 8 unfolds and inflates telescopically from its folded shape in an outward direction to form a radially extending spoke. Likewise, as shown in FIGS. 9, 10a, 10b and 10c, when spoke 8 is provided with compressible pleats 30, it can be easily compressed downward upon central tube 2 to reduce the stent's diametric profile. As shown in FIG. 9 in the un-inflated state each spoke 8 is compressed downward upon central tube 2 to form a canister-shaped element 33. Upon inflation, compressed spoke 8 unfolds and inflates upward from its compressed canister shape in an outward direction to form a radially extending spoke. Suitable materials for the above-described alternate embodiment spokes include elastic rubber or plastic, such as silicone rubber or polyether polyurethane. In another embodiment, stent 1 can comprise one or more of the preferred embodiment spokes and one or more of the alternate embodiment spokes described herein.

FIG. 11 shows the structures of the nasopharynx. As seen in FIG. 11, nasopharynx (nasopharyngeal cavity) 50 includes naris 54, nasal passageway 51, oropharynx 52, soft palate 56 and the area behind tongue base 57. More specifically, FIG. 11 shows the nasopharyngeal cavity of a patient suffering from sleep apnea due to prolapse of the soft palate 56. This condition, or any other obstruction of the nasopharyngeal cavity caused by growth, configuration, swelling or motility of the tissues, can be remedied by the method of using the present invention stent described herein. As shown in FIG. 12, un-inflated stent 1 of the present invention is inserted through the naris 54 and into the nasal passageway 51. Stent 1 is typically fully inserted when distal end 5 is pushed proximal to or just beyond the soft palate structures 56 of the oropharynx 52. In cases where the obstruction is due to lingual collapse, the stent may be inserted into position where its distal end is proximal to and presses against the base 57 of the tongue. When properly inserted in accordance with the apnea-causing condition, a portion of the device is proximal to the anatomic structure having the undesirable inflammation, configuration, growth or motility. In the full insertion mode proximal end 4 of tube 2 extends out through naris 54 leaving a sufficient length of the stent for manipulation and inflation.

In contrast to the prior art nasopharyngeal patency devices, the present invention stent requires no retaining mechanisms to maintain the stent in a collapsed (reduced diameter) state. However, the present invention stent can comprise such a mechanism. For example, stent 1 can be maintained in its un-inflated state whereby spokes 8 lie against central tube 2, for purposes of facilitating insertion by use of biocompatible low-tack adhesive disposed between spokes 8 and central tube 2 or between the folds or pleats of the alternate embodiment spokes. Upon inflation of the stent, the low-tack adhesive would release and allow spokes 8 to project radially outward from central tube 2. Alternatively, stent 1 can comprise a split sleeve surrounding the stent and holding spokes 8 against central tube 2. The sleeved stent could be inserted into the nasopharynx and the sleeve withdrawn out through the naris, leaving the stent in place. With the sleeve withdrawn, spokes 8 can be radially extended via inflation. As with prior art devices, the inflatable nasopharyngeal stent of the present invention can comprise an outer surface lubricant and anesthetic (either on the sleeve or stent itself) to aid in insertion and patient comfort.

Figure 13:
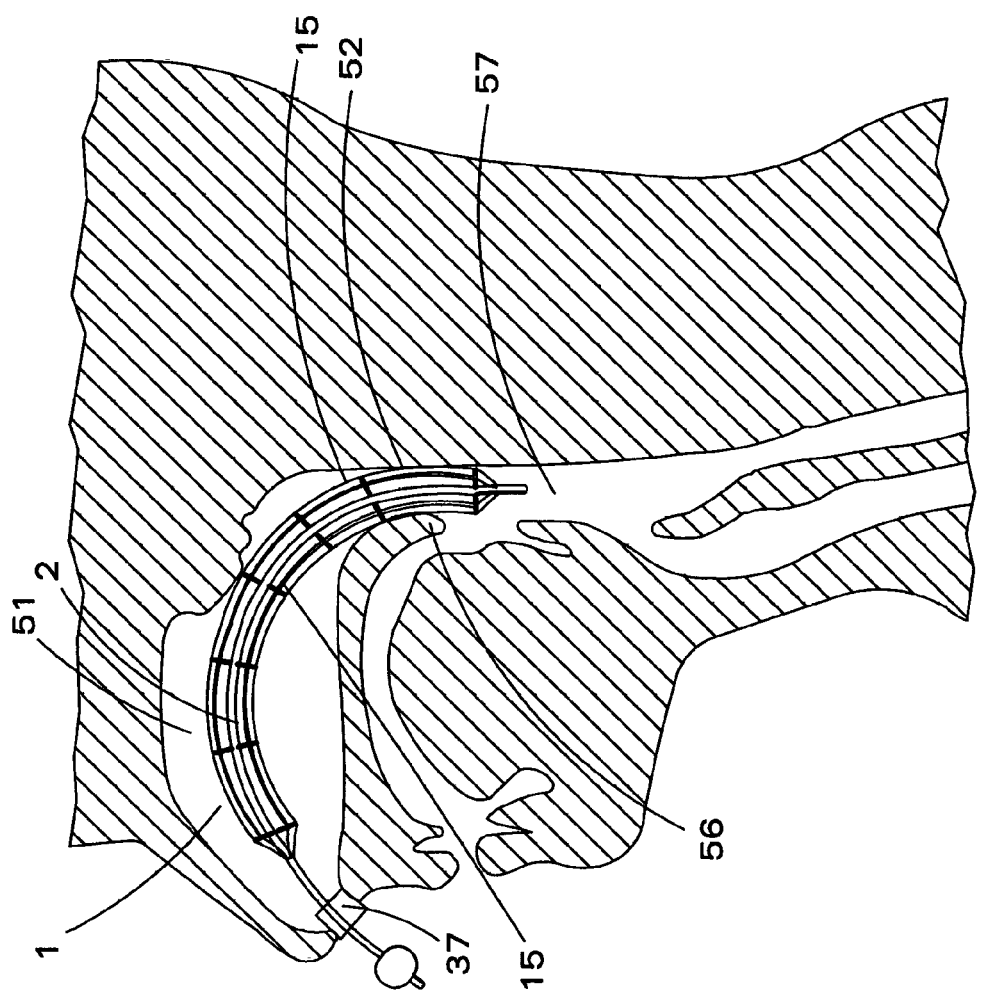
FIG. 13 is a cross section view of a nasopharyngeal cavity in which a preferred embodiment nasopharyngeal stent of the present invention is in place in its inflated state, eliminating the apnea causing obstruction of FIG. 11.

Once inserted to the proper location in the nasopharynx the stent can be inflated. Preferred inflation means disposed at the proximal end of the stent could include an integral elastic bulb pump, a receptacle adapted to receive a pump needle or an inflation port with automatic sealing. FIG. 13 is a cross section view of a nasopharyngeal cavity in which a preferred embodiment nasopharyngeal stent of the present invention is inserted in its inflated state. As shown in FIG. 13, inflated spokes 8 of preferred embodiment stent 1 radially project from central tube 2. By virtue of the inflation of spokes 8, perimeter ribs 15 and web members 23 are disposed outwardly remote from central tube 2 and press against the tissues of nasopharyngeal cavity 51. In particular, formerly prolapsed soft palate 56 shown in FIG. 11 is now held in place by ribs 15, web members 23 or both. By virtue of inter-spoke spaces 27, air may freely pass along stent 1 and through nasal passageway 51 into the oropharynx 52 resulting in airway patency. Additionally, the pressing action of perimeter ribs 15, web members 23 or both against the tissues of cavity 51, holds stent 1 in place. Thus, in contrast to the prior art nasopharyngeal patency devices, the present invention is designed for friction or compression fit within the nasopharynx. However, as added protection against aspiration of stent 1, stent 1 can include a fenestrated cuff 37 at proximal end 4. As compared to prior art devices, the scaffold-like, open structure of the stent allows for the reasonably unimpeded flow of secretions from the sinuses of the nasopharyngeal cavity.

The present invention stent is sized to allow comfortable insertion into the nasal passage. In this regard, the device may have an un-inflated diametric profile that will range practically from 5 to 10 millimeters in diameter. In the inflated state the diametric profile will range practically from 10 to 20 millimeters in diameter. Stent 1 can have a practical length that can range from 10 to 16 centimeters. Length and width will vary to accommodate varying nasopharyngeal dimensions among different patients. When properly inserted, distal end 5 should lie in the oropharynx 52, preferably proximal to or just beyond the soft palate 56 or tongue base depending upon the patient's condition. When inserted thusly, this leaves several centimeters of the proximal end 4 projecting from the nostril for manipulation and inflation. As with other prior art patency devices, the present invention inflatable nasopharyngeal stent can be adapted to be used in conjunction with other airway obstruction treatments such as CPAP.

While particular embodiments of the present invention have been illustrated and described herein, the present invention is not limited to such illustrations and descriptions. The embodiment shown and described is merely a preferred embodiment. It is apparent that changes and modifications may be incorporated and embodied as part of the present invention within the scope of the following claims. For example, the number of spokes 8 can be varied depending upon strength and flexibility demands. Similarly, inter-spoke spacings 27 can be numbered and sized to permit ancillary tubes (not shown) to be introduced for feeding, supplying oxygen or for suction.

What is claimed is:

1. A stent for treating anatomic occlusions of the nasopharynx and oropharynx, the stent comprising:
    an elongate central tube having a lumen, a first end and a second end;
    the first end including inflation means and the second end being closed;
    the central tube lumen defining a central inner chamber, the central inner chamber being in fluid communication with the inflation means;
    a plurality of spoke sets disposed along the central tube, each spoke set being located at a different position along the length of the central tube;
    each spoke set comprising one or more inflatable spokes;
    each inflatable spoke having an inner end, an outer end and being connected to the central tube at its inner end;
    each inflatable spoke further having a lumen defining a spoke inner chamber, the spoke inner chamber being in fluid communication with the central inner chamber;
    a plurality of ribs, each rib extending from an inflatable spoke of one spoke set to an inflatable spoke of at least one other spoke set;
    each rib having a proximal end, a distal end, a first side and a second side; and
    each rib having one or more web members extending from each of its first and second sides to an adjacent rib.

2. The stent of claim 1 wherein the plurality of spoke sets are arranged on the central tube such that the inflatable spokes of the plurality of spoke sets form one or more groupings of axially aligned spokes.

3. The stent of claim 1 wherein the plurality of spoke sets are arranged on the central tube such that the inflatable spokes of the plurality of spoke sets form one or more groupings of helically aligned spokes.

4. The stent of claim 1 further comprising an aligning lead extending from the distal end of each rib to the closed end of the central tube.

5. The stent of claim 1 further comprising an aligning lead extending from the proximal end of each rib to a point on the central tube between the spoke set closest the inflation means and the inflation means.

6. The stent of claim 1 wherein the inflation means comprises a bulb pump, a receptacle adapted to receive a pump needle or an inflation port with automatic sealing.

7. The stent of claim 1, which upon inflation further comprises wedge-shaped spaces between the spokes of one or more spoke sets.

8. The stent of claim 1 wherein the inflatable spokes lie flaccidly along the central tube when the stent is in its un-inflated state and upon inflation of the stent each inflatable spoke rigidifies, extends radially outward from the central tube at an angle approximately normal to the central tube and moves the rib attached to it outwardly from the central tube.

9. The stent of claim 8 wherein one or more inflatable spokes extend in an approximate longitudinal direction along the central tube when the device is an un-inflated state.

10. The stent of claim 1 wherein one or more inflatable spokes in the un-inflated state is foldable within itself such that it can be telescopically compressed into the central tube to reduce the stent's diametric profile and upon inflation of the stent the one or more foldable inflatable spokes inflate telescopically in an outward direction to form a radially extending spoke.

11. The stent of claim 1 wherein one or more inflatable spokes is provided with compressible pleats such that when the stent is in the un-inflated state, the one or more spokes with compressible pleats can be compressed downward upon the central tube to reduce the stent's diametric profile and upon inflation of the stent the one or more inflatable spokes with compressible pleats unfold and inflate upward in an outward direction to form a radially extending spoke.

12. The stent of claim 1 wherein one or more of the ribs or web members is an inflatable, fluidly connected extension of a spoke.

13. A method of treating a patient with an airway obstruction caused by undesirable inflammation, configuration, growth or motility of an anatomic structure of the nasopharynx, the method comprising:
providing the stent of any of claims 1 through 12 in an un-inflated state;
inserting said un-inflated stent into the patient's nasal passage via a naris so that a portion of the stent is proximal to the anatomic structure exhibiting the undesirable inflammation, configuration, growth or motility; and
inflating the stent such that one or more of the stent's ribs or web members press outwardly against the anatomic structure and upper airway patency is maintained.

* * * * *